United States Patent [19]
Barclay et al.

[11] Patent Number: 5,248,310
[45] Date of Patent: * Sep. 28, 1993

[54] ORAL OSMOTIC DEVICE WITH HYDROGEL DRIVING MEMBER

[75] Inventors: Brian L. Barclay; Jerry D. Childers, both of Sunnyvale; Jeri D. Wright, Dublin, all of Calif.; Virgil A. Place, Kawaihae, Hi.; Patrick S.-L. Wong, Palo Alto, Calif.

[73] Assignee: Alza Corporation, Palo Alto, Calif.

[*] Notice: The portion of the term of this patent subsequent to Jun. 4, 2008 has been disclaimed.

[21] Appl. No.: 859,191

[22] Filed: Mar. 27, 1992

[51] Int. Cl.[5] .............................................. A61K 9/22
[52] U.S. Cl. ............................. 604/891.1; 604/890.1; 424/468; 424/471; 424/473
[58] Field of Search ..................... 604/890.1–892.1; 424/468, 464, 471–473

[56] References Cited

U.S. PATENT DOCUMENTS

| | | | |
|---|---|---|---|
| 3,054,724 | 9/1962 | Roff et al. | 424/474 |
| 3,402,240 | 9/1968 | Cain et al. | 424/468 |
| 3,732,865 | 5/1973 | Higuchi et al. | 128/260 |
| 3,845,770 | 11/1974 | Theeuwes et al. | 128/260 |
| 3,854,480 | 12/1974 | Zaffaroni | 128/260 |
| 3,916,899 | 11/1975 | Theeuwes et al. | 128/260 |
| 4,111,202 | 9/1978 | Theeuwes | 128/260 |
| 4,238,475 | 12/1980 | Witzel et al. | 424/48 |
| 4,294,829 | 10/1981 | Suzuki et al. | 424/241 |
| 4,327,725 | 5/1982 | Cortese et al. | 128/260 |
| 4,478,822 | 10/1984 | Haslam et al. | 424/78 |
| 4,572,832 | 2/1986 | Kigasawa et al. | 424/19 |
| 4,612,008 | 9/1986 | Wong et al. | 604/892 |
| 4,627,971 | 4/1986 | Ayer | 424/15 |
| 4,639,368 | 1/1987 | Niazi et al. | 424/48 |
| 4,666,705 | 5/1987 | DeCrosta et al. | 424/482 |
| 4,713,243 | 12/1987 | Schiraldi et al. | 424/151 |
| 4,725,440 | 2/1988 | Ridgway et al. | 424/465 |
| 4,749,575 | 6/1988 | Rotman | 424/468 |

(List continued on next page.)

FOREIGN PATENT DOCUMENTS 0375063 12/1989 European Pat. Off. .
0391342 4/1990 European Pat. Off. .

OTHER PUBLICATIONS

"Treatment of Denture Stomatitis by a Sustained Drug-Delivery Device: a Preliminary Study", *J. Dent.*, (1988), vol. 16, pp. 219–221, D. J. Lamb and C. W. I. Douglas.

"Candidosis of the Oral Cavity, Recognition and Management", *Drugs*, vol. 36, pp. 633–642, (1988), K. D. Hay.

"Minor Aphthous Oral Ulcerations: A Double-Blind Cross-over Study of Beclomethasone Dipropionate Aerosol Spray", *Scot. Med. J.*, (1989), vol. 34, pp. 531–532.

"Treatment of Radiostomatitis with Salcoat", *Gan No Rinsho*, (1990), vol. 36, No. 1, pp. 66–90, Ishii, J. et al.

*Primary Examiner*—David Isabella
*Assistant Examiner*—Rob Clarke
*Attorney, Agent, or Firm*—Jean M. Duvall; D. Byron Miller; Edward L. Mandell

[57] ABSTRACT

An osmotic device (10) for delivering a beneficial drug, such as an anti-fungal, into the mouth of a human patient is disclosed. The device (10) has a size and shape adapting it to be comfortably retained in the mouth for extended periods of time. The device (10) comprises a wall (12) surrounding a compartment (13) housing a layer of an agent (14) that is insoluble to very soluble in aqueous biological fluids, e.g., saliva, and a layer (16) of a fluid swellable, hydrophilic polymer. A passageway (17) in the wall (12) connects the agent (14) with the exterior of the device (10). The wall (12) is permeable to the passage of aqueous biological fluid but substantially impermeable to the passage of the hydrophilic polymer (16). In one embodiment the beneficial agent (14) has a different color than the hydrophilic polymer (16). The wall (12) is sufficiently translucent to permit the patient to see the amount of drug/beneficial agent (14) remaining to be delivered. Marking lines (19) may be provided on the wall (12) indicating the amount of drug/agent (14) which has been delivered and/or the amount remaining to be delivered.

28 Claims, 2 Drawing Sheets

Cumulative Beclomethasone Dipropionate Released

U.S. PATENT DOCUMENTS

| | | | |
|---|---|---|---|
| 4,765,983 | 8/1988 | Takayanagi et al. | 424/434 |
| 4,783,337 | 11/1988 | Wong et al. | 424/468 |
| 4,786,503 | 11/1988 | Edgren et al. | 424/443 |
| 4,835,142 | 5/1989 | Suzuki et al. | 514/53 |
| 4,863,737 | 9/1989 | Stanley et al. | 424/440 |
| 4,871,548 | 10/1989 | Edgren et al. | 424/488 |
| 4,892,740 | 1/1990 | Takasima et al. | 424/474 |
| 4,946,685 | 8/1990 | Edgren et al. | 424/472 |
| 4,983,394 | 1/1991 | Hussein et al. | 424/465 |
| 5,021,053 | 6/1991 | Barclay et al. | 604/892.1 |
| 5,053,032 | 10/1991 | Barclay et al. | 604/892.1 |
| 5,178,866 | 1/1993 | Wright et al. | 424/471 |

Release Rate of Beclomethasone Dipropionate

FIG. 7

Cumulative Beclomethasone Dipropionate Released 5,248,310

ORAL OSMOTIC DEVICE WITH HYDROGEL DRIVING MEMBER

TECHNICAL FIELD

This invention pertains to an osmotic device for delivering a beneficial agent into the oral cavity of a patient. More particularly, the invention relates to an osmotic device comprising a shaped semipermeable wall surrounding a compartment containing a beneficial agent that is insoluble to very soluble in an aqueous fluid, and a layer of a water-swellable hydrophilic polymer driving member. A passageway through the wall connects the exterior of the device with an agent for delivering the agent from the device into the oral cavity. Means are provided for displaying the amount of agent remaining to be delivered.

BACKGROUND ART

Osmotic devices for delivering beneficial agents to environments of use are known to the prior art in U.S. Pat. Nos. 3,845,770 and 3,916,899 issued to Theeuwes et al. The osmotic devices disclosed in those patents comprise a semipermeable wall that surrounds a compartment containing an agent. The wall is permeable to the passage of an external fluid, and substantially impermeable to the passage of agent. There is a passageway through the wall for delivering the agent from the device. These devices release agent by fluid being imbibed through the wall into the compartment at a rate determined by the permeability of the wall and the osmotic pressure gradient across the wall to produce an aqueous solution containing agent that is dispensed through the passageway from the device. These devices are extraordinarily effective for delivering an agent that is soluble in the fluid and exhibits an osmotic pressure gradient across the wall against the fluid, and for delivering an agent that has limited solubility in the fluid and is admixed with an osmotically effective compound that is soluble in the fluid and exhibits an osmotic pressure gradient across the wall against the fluid. Devices of this type are typically designed to be swallowed or implanted to deliver a drug or other beneficial agent to the body.

In U.S. Pat. No. 4,111,202, the delivery kinetics of the device are enhanced by manufacturing the device with an agent compartment and an osmagent compartment separated by a film, which film is movable from a rested to an expanded state. The device delivers agent by fluid being imbibed through the wall into the osmagent compartment producing a solution that causes the compartment to increase in volume and act as a driving force that is applied against the film. This force urges the film to expand against the agent compartment and correspondingly diminish the volume of this compartment, whereby agent is dispensed through the passageway from the device. While this device operates successfully for its intended use, and while it can deliver numerous difficult to deliver agents, its use is somewhat limited because of the manufacturing steps needed for fabricating and placing the movable film in the device.

In U.S. Pat. No. 4,327,725, Cortese et al provided an osmotic dispensing device for delivering a beneficial agent which, because of its solubility in an aqueous biological fluid is difficult to deliver in meaningful amounts at controlled rates over time. The osmotic device of this patent comprises a semipermeable wall surrounding a compartment containing a beneficial agent that is insoluble to very soluble in an aqueous biological fluid and an expandable hydrogel. In operation, the hydrogel expands in the presence of external fluid that is imbibed into the device and in some operations mixes with the beneficial agents, thereby forming a dispensable formulation that is dispensed through the passageway from the device. This device operates successfully for its intended use, and it delivers many difficult to deliver beneficial agents for their intended purpose.

When administering a drug buccally (i.e., by absorption of the drug through the highly vascularized buccal tissues of the mouth) a number of conditions are present which make it difficult to effectively deliver drug in a therapeutically effective amount for a prolonged period of time (e.g., for periods greater than several minutes). For example, when a patient is given a drug-containing lozenge, there is a natural tendency to suck and chew on the lozenge thereby effectively reducing the time period during which the drug can be buccally administered by the lozenge. In addition, the action of saliva and swallowing by the patient effectively reduces the concentration of drug along the buccal membranes of the oral cavity and further causes much of the drug to be swallowed, in many cases rendering it inactive upon encountering the low pH environment of the stomach. This has been a particular problem in treating diseases of the mouth which require constant local administration of drug. One such disease condition is candidiasis of the oral cavity. A recent study has shown that 94% of male patients having acquired immuno-deficiency syndrome (AIDS) and 72% of those with AIDS-related complex (ARC) had oral candidiasis (Barr & Marder, AIDS: A Guide For Dental Practice, pp. 53–62, 1987). Recommended treatment of oral candidiasis is by repeated dosing of selected anti-fungal agents in the mouth, pharynx and esophagus. Typically, therapeutically recommended doses of nystatin, amphotericin B or miconazole, either in the form of liquid rinses or slowly dissolving pastilles and tablets have been used to treat oral candidiasis. Unfortunately, when the anti-fungal agents are administered by gargling or with rinses, the anti-fungal agents are cleared from the mouth in a matter of minutes. While the duration of drug delivery is increased somewhat using slowly dissolving pastilles and tablets, typically these release drug for no more than about 15 to 20 minutes. Accordingly, these dosage forms require frequent repetitive dosing (e.g., gargling every five minutes or taking a lozenge 3–4 times per hour) in order to effectively treat the condition.

Thus, there has been a clear need in the art of treating oral diseases, such as oral candidiasis, for a dosage form which is able to continuously deliver therapeutically effective amounts of drug or other beneficial agents into the oral cavity for extended periods of time, i.e. periods greater than about 15 to 20 minutes.

In response to the problem of short duration of drug delivery from rinses, pastilles and tablets, the use of an elementary osmotic pump to deliver medication to the buccal tissues has been suggested. Elementary osmotic pumps are typically formed by compressing a tablet of an osmotically active drug (or an osmotically inactive drug in combination with an osmotically active agent or osmagent) and then coating the tablet with a semipermable membrane which is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts the drug and/or salt to form a solution or suspension of the drug. The drug solution or suspension is then pumped out through the orifice as fresh fluid is imbibed through the semipermeable membrane.

While the use of elementary osmotic pumps has proven to be very successful in delivering drugs through the gastro-intestinal (GI) tract (i.e., by swallowing the elementary osmotic pump), there are several problems with buccal administration. As with drug-containing lozenges, there is a natural tendency for the patient to suck and chew on the drug-containing elementary osmotic pumps. Chewing in particular tends to compress the deformable membrane wall, thereby squeezing the drug solution or suspension out of the device at an accelerated rate. The duration of drug delivery is therefore severely curtailed. For example, when an elementary osmotic pump, designed to deliver drug at a relatively constant rate over a period of 12 to 24 hours within the GI tract, is placed in the oral cavity and subjected to patient sucking and chewing, the device delivers the entire drug dose relatively quickly, sometimes in less than about an hour.

Thus, there has been a need in the art of treating oral diseases for a dosage form which is osmotically driven but which is able to continuously deliver a drug within the mouth to the buccal membranes and which is relatively unaffected by the patient sucking and chewing on the device.

Another proposed solution to the problem of short duration of drug delivery from rinses, pastilles, and tablets, has been a delivery device comprised of a hydrophilic polymer having a drug dispersed therein. When placed between the cheek and gum of a patient, the hydrophilic polymer absorbs moisture from the buccal membrane, eventually adhering itself to the membrane surface. While it is desirable from the standpoint of patient comfort and convenience to adhere the delivery platform directly to the buccal membrane, this can create a problem when delivering a drug which has a tendency to cause irritation. When delivering an irritating drug, these devices tend to magnify the irritation since the device is adhered to the buccal membrane and maintains a high concentration of the irritating drug at a single membrane site.

Thus, there has been a need in the art of treating oral diseases for a dosage form which is able to continuously deliver a potentially irritating drug for extended periods of time without causing irritation.

Of course, with any dosage form designed to deliver a drug into the oral cavity for an extended period of time, means must be provided for alerting the patient when a predetermined dose of the drug has been delivered. For example, in cases where the recommended treatment is continuous delivery of drug into the mouth of the patient, a signaling means for alerting the patient when the entire dosage has been delivered is required. In the case of a dosage form designed to deliver a predetermined percentage of the dose buccally and the remainder of the dose through the GI tract, the dosage form must be provided with means for signaling the patient when the predetermined perecentage of the dose has been delivered.

DISCLOSURE OF THE INVENTION

Accordingly, it is an object of this invention to provide an osmotic device for the controlled delivery of a beneficial agent to the oral cavity of an animal, and in particular a human, for an extended period of time.

It is another object of the invention to provide an oral osmotic device useful for delivering an agent into the mouth of a patient, which agent is difficult to deliver and can be delivered by the subject device at a pharmaceutically effective rate and over an extended period of time.

It is another object of the invention to provide an oral osmotic device having a compartment containing an active agent that can be from insoluble to very soluble in an aqueous fluid which is present in the oral cavity, and an expandable driving member consisting of a layer of a hydrophilic polymer, which operates to diminish the volume occupied by the active agent, thereby delivering the agent from the device at a controlled rate over an extended period of time, the agent being released from the device in the form of a solution and/or suspension.

It is yet another object of the invention to provide an oral osmotic therapeutic device that can administer a complete pharmaceutical dosage of a very soluble or a poorly soluble agent, at a controlled and continuous rate into the mouth of an animal, for an extended delivery period and which device signals the animal when the complete dose of beneficial agent has been delivered.

It is a further object of the invention to provide an oral osmotic therapeutic device that can administer a complete pharmaceutical dosage of a very soluble, or a poorly soluble agent, at a controlled and continuous rate into the mouth of a human, for an extended delivery period and which device displays the amount of beneficial agent which has been delivered and the amount of beneficial agent which still remains in the device to be delivered.

It is a still further object of the invention to provide an oral osmotic therapeutic device that can administer a potentially irritating drug into the mouth of a human for an extended period of time without causing irritation to the buccal membrane.

Other objects, features, aspects and advantages of the invention will be more apparent to those versed in the art from the following detailed specification, taken in conjunction with the figures and the accompanying claims.

This invention concerns an osmotic device for controlled delivery of an active beneficial agent into the oral cavity of an animal, such as a human. The device comprises a wall formed of a material, which is permeable to the passage of an external aqueous fluid which is present in the oral cavity (e.g., saliva). The wall material may be either substantially impermeable or partially permeable to the passage of the active agent. The wall surrounds and forms a compartment that communicates with the exterior of the device through one or more passageways in the wall. The compartment contains an active agent exhibiting any degree of solubility in the aqueous fluid. For example, the agent may be soluble in the exterior fluid and exhibit an osmotic pressure gradient across the wall against the fluid, or the agent may be completely insoluble in the fluid and be admixed with an osmotic agent which exhibits an osmotic pressure gradient across the wall against the fluid. In either instance, the agent is next to the passageway. The compartment also contains a layer of an expandable driving member formed of a water-swellable hydrophilic polymer. The wall material is substantially impermeable to the hydrophilic polymer. The hydrophilic polymer absorbs fluid imbibed into the compartment, and can expand from a rested to an expanded state. The hydrophilic polymer is in contact with the agent formulation and positioned distant from the passageway. Agent is released from the device by the combined actions of fluid being imbibed through the wall into the compartment producing a solution or suspension containing agent, and by fluid being imbibed by the hydrophilic polymer causing it to expand and increase in volume, thereby exerting a force against the solution or suspension that decreases its volume, whereby the agent is released through the passageway at a rate controlled by the permeability of the wall, the osmotic pressure gradient across the wall, and the rate of expansion of the driving hydrophilic polymer over a prolonged delivery period. The device has a size and shape allowing it to be comfortably retained in the oral cavity for an extended period of time.

The device is provided with a mechanism for signaling the animal when the dose of beneficial agent has been delivered from the device. In one embodiment, the mechanism includes providing the layer of the beneficial agent with a taste which contrasts with the hydrophilic polymer layer taste. In a preferred embodiment, the layer of active agent contains a first flavoring agent while the hydrophilic polymer layer contains a second flavoring agent, having a flavor easily distinguishable from the flavor of the first flavoring agent. During use, the active agent is co-delivered with the first flavoring agent. The patient can easily recognize that the device is delivering drug due to the flavor of the first flavoring agent. Eventually, the entire dose of active agent is delivered. At this point, the device also stops delivering the first flavoring agent. Thereafter, the device begins delivering the hydrophilic polymer and the second flavoring agent. Upon tasting the second flavoring agent, the patient knows that the device has delivered the entire dose of beneficial agent.

In another embodiment, the mechanism for signaling the animal also displays the amount of beneficial agent present in the device. In a preferred embodiment, the active agent and the hydrophilic polymer have contrasting colors. The semipermeable wall is made sufficiently translucent to permit the patient to see the relative amounts of active agent and hydrophilic polymer present in the compartment.

BRIEF DESCRIPTION OF DRAWINGS

In the drawings (which are not drawn to scale) and the specification, like parts in related figures are identified by like numerals.

DETAILED DESCRIPTION OF THE INVENTION AND PREFERRED EMBODIMENTS

Turning now to the drawings, one example of an oral osmotic device is shown in FIGS. 1 through 4, and is indicated by the numeral 10. Device 10 is comprised of a wall 12 that surrounds and forms a compartment 13, as seen in the sectional views of FIGS. 3 and 4. Compartment 13 comprises a layer of a beneficial agent, identified by dots 14, that can be from insoluble to very soluble in an exterior aqueous fluid, indicated by dashes 15. When agent 14 is soluble in fluid 15, it exhibits an osmotic pressure gradient across wall 12 against the exterior fluid 15 imbibed into compartment 13. Compartment 13 in another embodiment contains a layer of agent 14 that has limited solubility or is substantially insoluble in fluid 15, and that exhibits limited, or it may not exhibit any, osmotic pressure gradient across wall 12 against the exterior fluid. When agent 14 has a limited solubility, or if it is substantially insoluble in fluid 15, it can be mixed with an osmagent that is soluble in the external fluid and exhibits an osmotic pressure gradient across wall 12 against the fluid. Wall 12 is formed of a polymeric material that is substantially permeable to the passage of the external fluid, and either impermeable or partially permeable to the passage of agent and osmagent. The polymer forming wall 12 is non-toxic and it maintains its physical and chemical integrity during the life of device 10.

Compartment 13 further houses a layer of an expandable driving member 16 composed of a hydrophilic polymer, optionally cross-linked, which possesses osmotic properties such as the ability to imbibe external fluid and exhibit an osmotic pressure gradient across the wall 12 against the fluid. Wall 12 is substantially impermeable to the passage of the hydrophilic polymer in driving layer 16. Layer 16 absorbs fluid imbibed into the compartment and swells. The osmotic pressure of the hydrophilic polymer network is the driving force of the swelling, expanding layer 16. Layer 16 is in contact with agent 14 and at the interface 18, formed by the hydrophilic polymer and the agent, a thin precipitate preferably forms. The precipitate is especially preferred when the active agent is soluble in the imbibed fluid. The precipitate forms in the presence of a solution containing the agent, or the agent and an osmagent, and it is substantially impervious and restricts the passage of agent 14 into layer 16. The precipitate further serves as an in situ formed membrane integral with the hydrophilic polymer for applying pressure against agent 14 during operation of device 10. When the active agent is substantially insoluble, interface 18 can be achieved simply by maintaining a difference in the viscosity values of layers 14 and 16. For example, layer 16 can be formulated with a hydrophilic polymer having a high molecular weight and a high degree of cross-linking. In such a case, there is negligible penetration of insoluble agent suspension into layer 16.

Device 10 releases agent 14 through one or more passageways 17 in wall 12 that communicates agent 14 with the exterior of device 10. Device 10 releases agent 14 by fluid being imbibed into compartment 13 in a tendency towards osmotic equilibrium at a rate determined by the permeability of wall 12 and the osmotic pressure gradient across wall 12. The imbibed fluid continuously forms a solution of the agent 14, or in cases where the agent 14 has limited or no solubility in the fluid, a solution of osmagent containing the agent 14 in suspension forms, which solution in either instance is released by the combined operation of device 10. These operations include the solution/suspension being osmotically delivered through passageways 17 due to the continuous formation of solution/suspension in the compartment 13, and by the hydrophilic polymer layer 16 swelling and applying pressure against the solution/suspension thereby delivering it to the exterior of device 10.

Compartment 13 operates to substantially insure that delivery of agent 14 from compartment 13 is constant over a prolonged period of time by two methods. First, hydrophilic polymer layer 16 operates to continuously concentrate agent 14 by imbibing some fluid from agent 14 to keep the concentration of agent 14 from falling below saturation. Secondly, layer 16 by imbibing external fluid 15 across wall 12 continuously increases its volume, as illustrated by the expansion of layer 16 from that shown in FIG. 3 to that shown in FIG. 4, thereby exerting a force on agent 14 and diminishing the volume of agent 14, thus concentrating agent 14 in compartment 13. The swelling of layer 16, along with the simultaneous, corresponding reduction of volume of agent 14, assures the delivery of agent 14 at a controlled rate over time.

Figure 1:
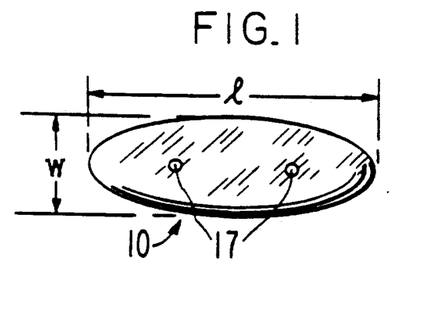
FIG. 1 is a top view of a preferred embodiment of an osmotic device for administering a beneficial agent into the oral cavity of an animal.
Figure 2:
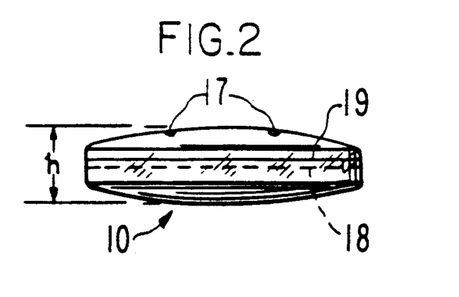
FIG. 2 is a side view of the oral osmotic device shown in FIG. 1.
Figure 3:
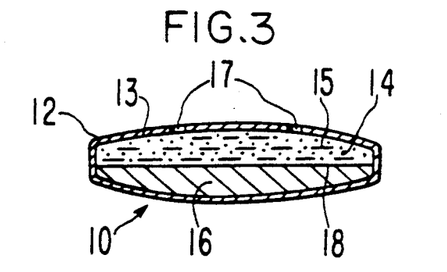
FIG. 3 is a side sectional view of the osmotic device of FIGS. 1 and 2 illustrating the internal structure of the device.

Device 10 of FIGS. 1-4 is designed for oral use, that is, for releasing either a locally or systemically acting therapeutic agent in the oral cavity of an animal, such as a human, over an extended period of time. Because the device is designed to be retained in the mouth for periods on the order of about 0.5 to 12 hours, the device must have an exterior shape which is comfortably retained in the mouth. It has been found that an oblong or elliptically shaped device 10 is preferred from a comfort standpoint. As shown in FIGS. 1 and 2, device 10 has a length l, a width w, and a height h. It has been found that devices 10 having an aspect ratio, which ratio is the ratio of l:w, of about 1.2:1 to about 3:1 are most comfortably retained in the mouths of humans. Preferably, the device 10 has an aspect ratio of about 1.3:1 to about 2:1, and most preferably about 1.5:1 to about 1.7:1. In addition, in order to fit comfortably between the cheek and gum of a patient, the device has a height of about 0.5 to about 10 mm, preferably about 2 to about 8 mm, and most preferably about 3 to about 5 mm. The device also has a volume of less than about 2 $cm^3$, preferably about 0.1 to about 0.5 $cm^3$, and most preferably about 0.25 $cm^3$.

Osmotic delivery device 10 has a mechanism for displaying the amount of drug formulation remaining in the device for delivery into the patient. In one preferred embodiment, the display means comprises color contrast between the drug formulation 14 and the driving layer 16, in combination with a translucent wall 12. In this embodiment, the color of the drug formulation 14 is chosen to provide good visual contrast with the color of the driving layer 16. The color of the drug formulation 14 can be achieved using any number of coloring techniques known in the art. For example, the drug itself may have a natural color which itself adequately contrasts with the natural color of the driving layer 16. On the other hand, a number of pharmaceutically acceptable dyes or coloring agents may be mixed with either the drug formulation 14 and/or the driving layer 16, in order to provide the appropriate color contrast. Suitable pharmaceutically acceptable coloring agents, both natural and synthetic, are known in the art. See Remington's Pharmaceutical Sciences, 14th Ed., pp 1,319–1,321.

In accordance with this embodiment of the invention, the patient can easily determine the amount of agent 14 remaining in compartment 13 simply by visually inspecting device 10. For example, the drug formulation 14 may have a white color and the layer 16 may be dyed to achieve a red color. When the device is first placed in the mouth of the patient, the white and red layers are clearly visible through the translucent semipermeable wall 12. After a period of time in the patient's mouth, the device 10 will imbibe aqueous fluid (e.g., saliva) thereby causing a solution or suspension of the drug 14 to be formed and also causing the hydrogel 16 layer to expand. Because the drug layer and the hydrophilic polymer layer have contrasting colors, the patient can easily determine the relative amount of drug remaining in the device for delivery. This can have a number of useful applications. For example, in treating a condition requiring substantially continuous delivery of drug to the oral cavity, the patient is alerted when the device 10 has delivered all of the drug. At this point, only the red hydrophilic polymer layer remains. This can be checked simply by visually inspecting the device.

In another embodiment, the device of the present invention can be used to extend the absorption period of a drug which might be poorly absorbed throughout certain portions of the GI tract, such as the colon. In such a case, it may be desirable to administer a predetermined percentage of a dose of the drug buccally followed by delivery of the remaining dose of drug in the device within the GI tract. One example of such a drug is captopril, an anti-hypertensive used for the treatment of heart disease. Another example is the drug cimetidine, a histamine $H_2$ receptor antagonist used for the treatment of duodenal and gastric ulcers. In such cases, the device 10 may be provided with a mark or line 19 on the external surface of wall 12 (See FIG. 2). The position of the line 19 corresponds to the delivery of the predetermined percentage of the dose from the device 10. Thus, when the interface 18 between the hydrophilic polymer layer 16 and drug 14 layers becomes aligned with the exterior line 19 on wall 12, the patient is alerted to the fact that the predetermined percentage of the dose of drug has been delivered. At this point, the patient simply swallows the device and the remaining portion of drug in device 10 is administered through the GI tract.

In another embodiment, a plurality of lines 19 are provided on wall 12. Each of the lines 19 is positioned to align with interface 18 after the device 10 has been retained in the mouth for a predetermined period of time, e.g., a one hour marking line, a two hour marking line, etc. In this way, the patient can easily monitor the duration of drug delivery, even without access to a clock.

In another preferred embodiment of the present invention, the mechanism for signaling the patient comprises a contrast in taste between the drug formulation 14 and the hydrophilic polymer driving layer 16. In this embodiment, the flavor of the drug formulation 14 is chosen to provide a sharp contrast with the flavor of the hydrophilic polymer driving layer 16. Preferably, the drug formulation contains a flavoring agent which is enjoyed by the patient, while the hydrophilic polymer layer contains a flavoring agent having an unpleasant taste. For example, the drug can be flavored with peppermint oil while the hydrophilic polymer layer is flavored with a salt (e.g., NaCl). The flavor of the drug formulation 14 can be achieved by any number of flavoring techniques known in the art. For example, the drug itself may have a natural flavor which itself adequately contrasts with the natural flavor of the hydrophilic polymer driving layer 16. On the other hand, a number of pharmaceutically acceptable flavoring agents may be mixed with either the drug formulation 14 and/or the hydrophilic polymer in layer 16 in order to provide the appropriate taste contrast. Suitable pharmaceutically acceptable flavoring agents, both natural and synthetic, are known in the art. See Remington's Pharmaceutical Sciences, 14th Ed., pp 1,321–1,338.

In another preferred embodiment of the present invention, a flavoring agent is incorporated in the wall 12. Preferably, the wall 12 contains a flavoring agent which leaches out into the saliva as soon as the device 10 is placed in the patient's mouth. Most preferably, the wall 12 contains a flavoring agent which is enjoyed by the patient and, in particular, can be the same flavoring agent used to flavor the drug formulation 14. In general, the wall 12 will contain up to about 20 wt % flavoring agent. Any of the pharmaceutically acceptable flavoring agents mentioned above may be incorporated into wall 12.

Osmotic delivery device 10 can be manufactured with a wall 12 formed of a material that does not adversely affect the agent 14 (e.g., a drug), the osmagent, if any is present, and the hydrophilic polymer in layer 16. The material forming wall 12 should also not adversely affect the buccal tissues of the patient. In addition, the material forming wall 12 is permeable to the passage of an external aqueous fluid 15, such as water and biological fluids naturally present in the oral cavity (e.g., saliva), while remaining essentially impermeable to the passage of hydrophilic polymer, and optionally impermeable to the passage of agents, including drugs, osmagents, and the like. The selectively semipermeable materials forming wall 12 are insoluble in fluids naturally present in the oral cavity. Typical materials for forming wall 12 include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminacetate, cellulose acetate ethyl carbamate, cellulose acetate chloracetate, cellulose dipalmatate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21% to 35%, cellulose triacetate having a degree of substitution of 2 to 3 and an acetyl content of 35% to 44.8%, as disclosed in U.S. Pat. No. 4,160,020. Generally, semipermeable materials having a fluid permeability of $10^{-5}$ to $10^{-1}$ (cc.mil/cm$^2$.hr atm) expressed per atmosphere of hydrostatic or osmotic pressure difference across semipermeable wall 12 can be used for forming wall 12.

In accordance with one preferred embodiment of the present invention, at least a portion of the material forming wall 12 is sufficiently translucent to allow a patient to see the relative amounts of hydrophilic polymer 16 and drug 14 remaining in compartment 13. Examples of suitable translucent materials include the cellulosic polymers mentioned above. Generally, the wall 12 will contain a sufficient amount of translucent material to enable the patient to see the drug layer 14 and the hydrophilic polymer layer 16 within compartment 13. Suitable amounts of translucent materials will depend upon the translucency of the wall material, the methods and conditions under which the wall materials are formed, as well as the amount of contrast in the colors of the drug and hydrogel layers. Suitable amounts of translucent materials can be easily determined through routine experimentation using the examples herein.

The expression "active agent", as used herein, includes any beneficial agent or compound that can be delivered from the device into the oral cavity to produce a beneficial and useful result. The agent can be insoluble to very soluble in the exterior fluid. For example, the agent can be very soluble in fluid 15 that enters compartment 13 and function as its own osmotically effective solute, or it can be poorly soluble in the fluid and be mixed with an osmotically effective compound that is soluble in the fluid for delivering an agent from the device.

In the specification and the accompanying claims, the term "agent" includes drug, and the term "drug" includes any physiologically or pharmacologically active substance that produces a local or systemic effect when administered to the oral cavity of a human. The term "physiologically", as used herein, denotes the administration of a drug to produce normal levels and functions. The term "pharmacologically" denotes variations in response to amount of drug administered to the host. Stedman's Medical Dictionary, 1966, published by Williams and Wilkins, Baltimore, Md. The active drug that can be delivered includes inorganic and organic drugs without limitations, those drugs that act on the central nervous system, depressants, hypnotics, sedatives, psychic energizers, tranquilizers, anticonvulsants, muscle relaxants, anti-Parkinson agents, analgesics, anti-inflammatory, local anesthetics, muscle contractants, anti-microbials, anti-fungals, anti-malarials, hormonal agents, contraceptives, sympathomimetics, diuretics, anti-parasitics, neoplastics, hypoglycemics, ophthalmics, electrolytes, diagnostic agents, and cardiovascular drugs.

Exemplary drugs that are very soluble in water and can be delivered by the devices of this invention include nystatin, chlorhexidine, clonidine, sodium fluoride, prochlorperazine adisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, and the like.

Exemplary drugs that are poorly soluble in water and that can be delivered by the devices of this invention include nicotine base, retin A, ibuprofen, diphenidol, meclizine hydrochloride, prochlorperazimine maleate, phenoxybenzamine, thiethylperazine maleate, anisindone, diphenadione erythrityl tetranitrate, dizoxin, isofuraphate, reserpine, acetazolamide, methazolamide, bendroflumethiazide, chlorpropamide, tolzamide, chlormadinone acetate, phenaglycodol, allopurinol, aluminum aspirin, methotrexate, acetyl sulfisoxazole, erythromycin, progestins, esterogenic progestational hormones, corticosteroids, beclomethasone dipropionate, hydrocortisone, hydrocorticosterone acetate, cortisone acetate, triamcinolone, testosterone, testosterone esters, methyltesterone, 17$\beta$-estradiol, ethinyl estradiol, ethinyl estradiol 3-methyl ether, prednisolone, 17$\beta$-hydroxyprogesterone acetate, 19-nor-progesterone, norgestrel, norethindone, norethiderone, progesterone, norgesterone, norethynodrel, and the like.

The term "beclomethasone dipropionate" is used to designate both the actual compound and the related compounds thereof. While the preferred active agent according to the present invention is beclomethasone dipropionate itself, the invention also includes analogs, homologs, agonists, antagonists and other compounds related to beclomethasone dipropionate. Numerous analogs, homologs, agonists, antagonists and other compounds related to beclomethasone dipropionate are known in the art, representatives of which are disclosed in, for example, GB Patents Nos. 912,378 and 901,093, which are incorporated by reference.

Examples of other drugs that can be delivered by the osmotic device include aspirin, indomethacin, naproxen, fenoprofen, sulidac, diclofenac, ibuprofen, indoprofen, nitroglycerin, propranolol, metoprolol, valproate, oxprenolol, timolol, atenolol, alprenolol, cimetidine, clonidine, imipramine, levodopa, chlorpromazine, reserpine, methyl-dopa, dihydroxyphenylalanine, pivaloyloxyethyl ester of $\alpha$-methyldopa hydrochloride, theophylline, calcium gluconate, ferrous lactate, vincamine, diazepam, phenoxybenzamine, $\alpha$-blocking agents, polypeptides, proteins, insulin and the like. The beneficial drugs are known to the art in *Pharmaceutical Sciences*, by Remington 14th Ed., 1979, published by Mack Publishing Co., Easton, Pa.; *The Drug, The Nurse, The Patient, Including Current Drug Handbook*, 1974–1976, by Falconer, et al., published by Saunder Company, Philadelphia, Pa.; and *Medicinal Chemistry*, 3rd Ed., Vol. 1 and 2, by Burger, published by Wiley-Interscience, N.Y.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. Drugs in the form of polypeptides and proteins, which are susceptible to being broken down in the GI tract, can also be delivered systemically by the device of the present invention by absorption through the buccal membranes of the oral cavity.

In order to withstand the conditions of use within the oral cavity (i.e., patient sucking the delivery device), the drug layer 14 should contain a gelling or suspending agent which prevents the exterior wall from collapsing during use. Representative gelling or suspending agents include acacia, agar-agar, calcium carrageenan, kappa carrageenan, alginic acid, algin, agarose powder, collagen, colloidal magnesium silicate, colloidal silicon dioxide, sodium carboxy methyl cellulose, partially cross-linked polyacrylic acid, polyvinyl pyrrolidone, hydroxyethyl cellulose, hydroxypropyl cellulose, hydroxypropylmethyl cellulose, polyethylene oxide, pectin, gelatin, calcium silicate and mixtures thereof.

Generally, the drug layer 14 typically contains from about 0.5 to about 99.9 wt % of a gelling or suspending agent, depending on the loading of drug/beneficial agent in layer 14 and its solubility in the fluid entering the device. Most preferably, the gelling or suspending agent is polyethylene oxide, hydroxy propyl methyl cellulose or mixtures thereof.

The agent including drug, can also be present in the compartment with a binder, dispersant, wetting agent and lubricant. Representative of these include binders like polyvinyl pyrrolidone, and hydroxypropyl methyl cellulose, wetting agents such as fatty amines and fatty quaternary ammonium salts, and lubricants such as magnesium stearate and stearic acid. The phrase drug formulation indicates the drug is present in the compartment accompanied by a gelling or suspending agent, an osmagent, a binder, dye or the like.

The amount of agent initially present in the device is not critical, however it is preferred to initially provide an amount of active agent, which agent is soluble in fluid entering the device, in excess of the amount that can be dissolved in the fluid that enters the device. Under this physical state, when the agent is in excess, the device will osmotically operate to give a substantially constant rate of release. Generally, the device can house from about 0.05 ng to 500 mg or more of drug, carrier, fillers, excipients, etc. with individual devices containing for example, 25 ng, 1 mg, 5 mg, 125 mg, 250 mg, 500 mg, and the like.

When beclomethasone dipropionate is the agent 14 employed in device 10, the device can contain about 0.01 mg to about 6 mg beclomethasone dipropionate. Preferably, the device contains about 0.1 mg to about 1.0 mg of beclomethasone dipropionate. The release rate of beclomethasone dipropionate from the device can range from about 0.01 mg/hr to about 0.5 mg/hr over the extended delivery period. Preferably, the device releases beclomethasone dipropionate at the rate of about 0.02 mg/hr to about 0.1 mg/hr over the extended delivery period. The device, containing beclomethasone dipropionate, can be administered to the patient one to six times a day, preferably one to two times a day.

The osmagent present in the device, when used according to the mode of the invention where the beneficial agent is not itself osmotically active, is an osmotically effective compound soluble in the fluid that enters the device that exhibits an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glycose, hydrophilic polymers such as cellulose polymers, mixtures thereof, and the like. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher.

The hydrophilic polymers suitable for layer 16 of the invention are swellable, hydrophilic polymers which interact with water and aqueous biological fluids and swell or expand to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be noncross-linked or cross-linked. The swellable, hydrophilic polymers are, in one presently preferred embodiment, lightly cross-linked, such cross-links being formed by covalent ionic bonds or hydrogen bonds. The polymers can be of plant, animal or synthetic origin. Hydrophilic polymers suitable for the present purpose include poly(hydroxy alkyl methacrylate), having a molecular weight of from 30,000 to 5,000,000; poly(vinylpyrrolidone) having moleuclar weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose; cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

Other polymers include polymers that form hydrogels, such as Carbopol® acidic carboxy polymers, having a molecular weight of 450,000 to 4,000,000; Cyanamer® polyacrylamides; cross-linked water sweallable indene-maleic anhydride polymers, Goodrite® polyacrylic acid having a molecular weight of 80,000 to 200,000; Polyox® polyethylene oxide polymers having molecular weight of 100,000 to 5,000,000 and higher; starch graft copolymers; Aqua-Keeps® acrylate polymer polysaccharides composed of condensed glucose units, such as diester cross-linked polyglucan, and the like. Representative polymers that form hydrogels are known to the prior art in U.S. Pat. Nos. 3,865,108 issued to Hartop; 4,002,173 issued to Manning; 4,207,893 issued to Michaels; and in *Handbook of Common Polymers*, by Scott and Roff, published by the Chemical Rubber Company, Cleveland, Ohio.

For the purpose of the invention, the phrase agents with degrees of solubility, as used herein, indicates agents that are insoluble to very soluble in aqueous biological fluids present in the oral cavity, such as saliva. Further for this purpose, an insoluble agent indicates a solubility of less than 25 mg of agent per ml of fluid, a poorly soluble agent is one that dissolves in the range of about 25 mg to 150 mg of agent per ml of fluid, a soluble agent dissolves about 150 mg to 600 mg of agent per ml of fluid. While the presently preferred embodiments have been described with reference to poorly or very soluble agents, it is to be understood the device can be used to deliver other agents.

Typical methods used for the measurement of solubility are chemical and electrical conductivity. Details of various methods for determining solubilities are described in *United States Public Health Service Bulletin*, No. 67 of the Hygienic Laboratory; *Encyclopedia of Science and Technology*, Vol. 12, pages 542 to 556, 1971, published by McGraw-Hill, Inc,; and *Encyclopedia Dictionary of Physics*, Vol. 6, pages 547 to 557, 1962, published in Pergamon Press, Inc.

Figure 4:
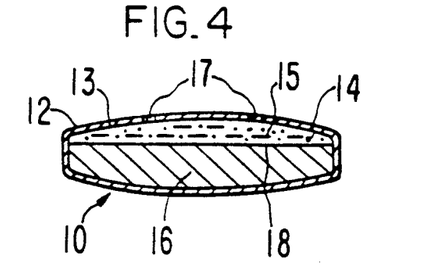
FIG. 4 is a side sectional view of the osmotic device of FIG. 3 after delivering a portion of the beneficial agent from the device.

The interaction of the hydrophilic polymer-drug interface can be ascertained by placing a film formed of a hydrophilic polymer in contact with an aqueous solution containing an active agent, and sometimes an osmagent, and observing the modification of the polymer at the polymer-aqueous environment. The surface of the polymer should be modified in situ during operation of the device. If a precipitate forms along the outer surface of the polymer, the polymer and the solution are suitable for operating the compartment of the device. A representative procedure that can be used consists in measuring the percent weight gain for various polymers immersed in a saturated solution of a drug or an osmagent. The procedure broadly indicates interface absorption activity. That is, if there is little absorption by the polymer, there is correspondingly little gain in weight and the polymer is suitable for the purpose. Similarly, if there is a large gain in weight indicating a large volume absorbed, the polymer is not preferred for the purpose. FIG. 4 of U.S. Pat. 4,327,725 represents the percent weight gain for four polymers (A is Klucel H ® polymer; B is Polyox COAG ® polymer; C is Carbopol-934 ® polymer; and D is Na Carbopol-934 ® polymer) immersed in a saturated solution of NaCl as a function of the imbibition pressure of the polymer. Polymer imbibition pressure of any given hydrophilic polymer can be determined according to the procedure outlined in Cortese et al., U.S. Pat. No. 4,327,735, column 10, line 67 to column 12, line 24, which is incorporated herein by reference.

The device of the invention is manufactured by standard techniques. For example, in one embodiment, the agent and other ingredients that may be housed in one area of the compartment adjacent to the passageway, are pressed into a solid possessing dimension that corresponds to the internal dimensions of the area of the compartment the agent will occupy, or the agent and other ingredients and a solvent are mixed into a solid or semisolid form by conventional methods such as ball-milling, calendering, stirring or rollmilling, and then pressed into a preselected shape. Next, a layer of a hydrophilic polymer is placed in contact with the layer of agent in a like manner, and the two layers are surrounded with a semipermeable wall. The layering of agent formulation and hydrophilic polymer can be fabricated by conventional two-layer press techniques. The wall can be applied by molding, spraying or dipping the pressed shapes into a wall forming material. Another and presently preferred technique that can be used for applying the wall is the air suspension procedure. This procedure consists of suspending and tumbling the pressed agent and dry hydrophilic polymer in a current of air and a wall forming composition until the wall is applied to the agent-hydrophilic polymer composite. The air suspension procedure is described in U.S. Pat. No. 2,799,241; *J. Am. Pharm. Assoc.*, vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, Fourteenth Edition, pages 1,626 to 1,678, 1970, published by Mack Publishing Company, Easton, Pa.

Exemplary solvents suitable for manufacturing the wall include inorganic and organic solvents that do not adversely harm the wall forming material, and the final device. The solvents broadly include members selected from the group consisting of aqueous solvents, alcohols, ketones, esters, ethers, aliphatic hydrocarbons, halogenated solvents, cycloaliphatic, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglycol methyl ether, water and mixtures thereof such as acetone and water, acetone and methanol, acetone and ethyl alcohol, methylene dichloride and methanol, and ethylene dichloride and methanol, and mixtures thereof.

The expression "passageway", as used herein, comprises means and methods suitable for releasing the agent from the system. The expression includes one or more aperture, orifice or bore through wall 12 formed by mechanical procedures, or by eroding an erodible element, such as a gelatin plug, in the oral cavity. In cases where the semipermeable membrane is sufficiently permeable to the passage of beneficial agent/drug, the pores in the membrane may be sufficient to release the agent/drug in therapeutically effective amounts. In such cases, the expression "passageway" refers to the pores within the membrane wall even though no bore or other orifice has been drilled therethrough. A detailed description of osmotic passageways and the maximum and minimum dimensions for a passageway are disclosed in U.S. Pat. Nos. 3,845,770 and 3,916,899, the disclosures of which are incorporated herein by reference. Preferably, one to two passageways 17 are provided in device 10 as shown in the Figures.

The expressions "extended period of time" and "extended delivery period", as used herein, generally refer to periods greater than about 0.5 hours, preferably about 0.5 to 12 hours, more preferably about 0.5 to 6 hours, most preferably about 1-4 hours.

The following examples are merely illustrative of the present invention and should not be considered as limiting the scope of the invention in any way.

EXAMPLE 1

An osmotic therapeutic device for the controlled and continuous release into the oral cavity of the beneficial antifungal drug nystatin was made as follows: 43 mg of nystatin, 193 mg of polyethylene oxide (Polyox N-10), 13 mg of hydroxy propyl methyl cellulose (HPMC E-5), 3 mg of sodium saccharin, 13 mg of oil of anise and 1 mg of magnesium stearate are mixed thoroughly and pressed in a Manesty ® Layer Press with a ⅜ inch oval punch using a pressure head of 2 tons to produce a layer of the drug composition. The nystatin had a natural yellow color, while the remaining ingredients had a natural white color. Accordingly, the drug composition had a natural pale yellow color. The oil of anise was added as a flavoring agent to mask the objectionable bitter taste of the nystatin.

Next, the driving layer of the device was formulated by mixing 114 mg of polyethylene oxide (Polyox Coag), 52 mg NaCl, 9 mg hydroxy propyl methyl cellulose (HPMCE-5), 2 mg $Fe_2O_3$ as a colorant and 1 mg of magnesium stearate. The formulation was added to the Manesty Layer Press and pressed to form a layer of hydrophilic polymer in contact with the drug layer. The hydrophilic polymer driving layer had a reddish-brown color due to the ferric oxide.

Figure 5:
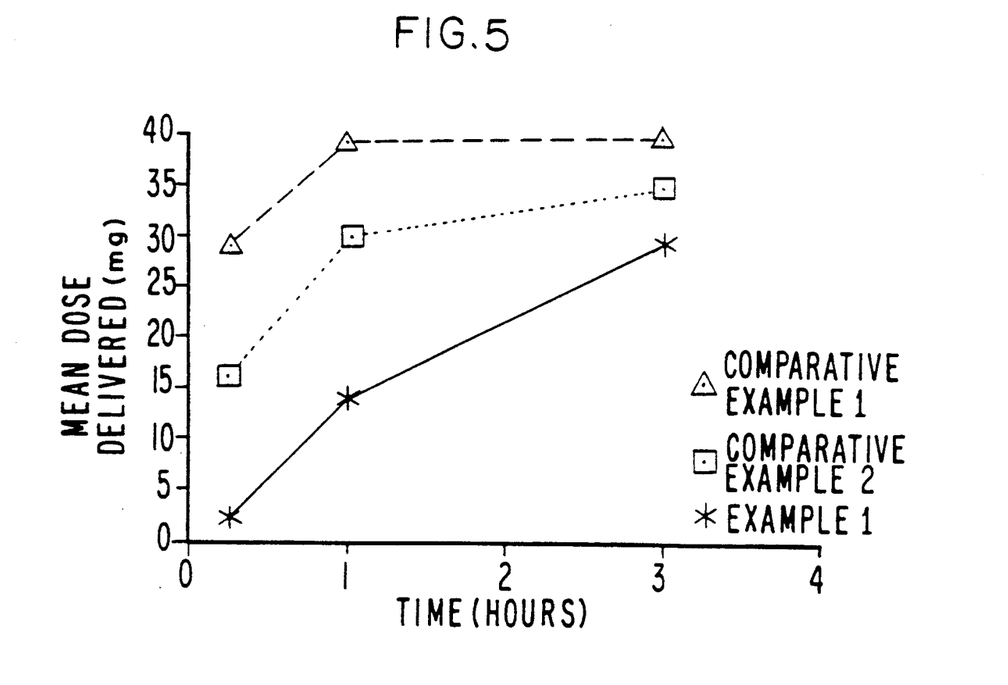
FIG. 5 is a graph depicting the cumulative amount of beneficial agent released from (i) a device according to the present invention and (ii) two prior art delivery devices.

Next, a semipermeable wall was formed by blending 24 g of cellulose acetate having an acetyl content of 39.8% with 1,103 ml of acetone, 97 ml of water and 16 g of hydroxy propyl cellulose (KLUCEL EF), and spray coating the two layered compartment forming member in an air suspension machine having a 0.4 kg charge until a 6 mil thick semipermeable wall surrounds the compartment. The coated device was dried for 72 hours at 35° C., and then two 25 mil passageways were laser drilled through the semipermeable wall to connect the layer of drug with the exterior of the device. The KLUCEL component of the wall material made the wall sufficiently translucent to clearly see the yellow drug layer and the reddish-brown hydrophilic polymer layer. Accompanying FIG. 5 depicts the cumulative amount of nystatin released by the device when retained in the mouth of a human over a period of 3 hours and compares the nystatin release profile with the profiles of the nystatin delivery devices described in Comparative Examples 1 and 2.

COMPARATIVE EXAMPLE 1

A chewing gum containing nystatin is prepared in accordance with Example 1 of U.S. Pat. No. 4,238,475 with the following exceptions. Each stick of gum is loaded with 43 mg of nystatin (the same dose of nystatin utilized in Example 1) instead of 5 mg nystatin. Thus, the weight percent of nystatin in each stick of chewing gum is about 1.5 weight percent ("wt %") rather than 0.18 wt %. All other ingredients are prepared as in Example 1 of U.S. Pat. No. 4,238,475. Accompanying FIG. 5 depicts the cumulative amount of nystatin released into the mouth of a human chewing the gum over a period of 3 hours.

COMPARATIVE EXAMPLE 2

A nystatin containing chewing gum is prepared as in comparative Example 1, except that the conventional chewing gum base is replaced with ethylene vinyl acetate having a vinyl acetate content of 51%. The dose of nystatin in each stick of gum is again 43 mg or about 1.5 wt %. The gum is chewed by a human for a period of 3 hours and the cumulative amount of nystatin released is shown in FIG. 5.

A comparison of the three nystatin delivery profiles plotted in FIG. 5 shows that the device of the present invention releases nystatin into the oral cavity at a substantially constant delivery rate. This is shown by the substantially straight line release profile for Example 1. By comparison, the chewing gums of Comparative Examples 1 and 2 have a tendency to release a major portion of the nystatin within the first 20 minutes of chewing. For Comparative Example 1, the chewing gum releases about 75% of the total nystatin dose in the first 20 minutes. For the EVA base gum of Comparative Example 2, approximately 40% of the nystatin dose is delivered within the first 20 minutes. The curves shown in FIG. 5 illustrate that the chewing gums of Comparative Examples 1 and 2 are ill-suited for delivering nystatin to the oral cavity over periods of greater than about 1 hour.

EXAMPLE 2

An osmotic therapeutic device manufactured in the form of an oral delivery device for delivering chlorhexidine diacetate into the oral cavity was manufactured as follows: first a 150 mg composition comprising 3.7% chlorhexidine diacetate, 90.8% polyethylene oxide (Polyox N-10), 5% hydroxy propyl methyl cellulose (HPMC E-5) and 0.5% magnesium stearate was prepared by blending the four ingredients into a homogenous blend, and then pressed into a solid mass in a commercially available Manesty tableting machine set to a Stoke's hardness of 7 kg. The resulting drug-containing layer had a white color.

Next, a 100 mg composition comprising 68.5% polyethylene oxide having a molecular weight of about 5,000,000 (Polyox Coag), 20% NaCl, 5% HPMC E-5, 5% Carbomer 934 P, 1% ferric oxide colorant and 0.5% magnesium stearate was added to the tableting machine and pressed into a solid mass in contact with the drug-containing layer. The hydrophilic polymer layer had a reddish-brown color, due to the ferric oxide, providing a good color contrast with the white drug-containing layer. Then, the two layered mass was coated in a standard air suspension machine with a semipermeable polymeric wall formed from a 4% solids solution consisting of 60 wt % cellulose acetate having an acetyl content of 39.8%, in a solvent consisting of 90% acetone and 10% water, and 40 wt % hydroxy propyl cellulose (KLUCEL EF). The resulting semipermeable wall had a thickness of 5 mils. The KLUCEL component of the wall material made the wall translucent, making it possible to see both the white drug-containing layer and the reddish-brown hydrogel layer within the inner compartment of the device. Finally, one osmotic passageway, having a diameter of 25 mils, was drilled through the wall facing the chlorhexidine-containing layer for delivering it from the device.

EXAMPLE 3

An oral osmotic therapeutic device for delivering ibuprofen is manufactured by following the procedure of Example 2, with all conditions and procedures as described, except in this example the layer of drug formulation comprises 20.5% ibuprofen, 66.5% Polyox N-10, 5% HPMC E-5, 7.5% sodium carbonate and 0.5% magnesium stearate. The ibuprofen containing layer has a white color. The hydrophilic polymer layer comprises 64.3% Polyox Coag, 29.2% NaCl, 5% HPMC E-5, 1% ferric oxide colorant, and 0.5% magnesium stearate. The resulting hydrogel layer has a reddish-brown color. The translucent semipermeable wall is 5 mils thick and comprises 60% cellulose acetate having an acetyl content of 39.8% and 40% Klucel EF, formed from a solvent consisting essentially of 90% acetone and 10% water. One passageway with a diameter of 25 mils is drilled in the side of the device adjacent the ibuprofen-containing layer.

Unlike in Example 2, following drilling of the passageway, the device is overcoated with a mixture comprising 20 wt % ibuprofen and 80 wt % HPMC. The overcoating layer has a thickness of 3 mils. The ibuprofen containing overcoat provides a loading dose which is quickly delivered to the patient upon retention in the mouth. Generally, the overcoat layer will be completely removed by patient sucking within about 15 to 30 minutes. This is especially useful in cases where there is an initial delay between the time when the device is placed in the mouth of the patient and the time when the device begins pumping drug.

EXAMPLE 4

An osmotic therapeutic device for the controlled and continuous release of nystatin into the oral cavity is made as follows. The drug formulation layer comprises 30 wt % nystatin, 50 wt % Polyox N-10, 18 wt % spearmint oil, 1 wt % sodium saccharin and 1 wt % magnesium stearate. The ingredients are mixed thoroughly and pressed in a Manesty ® Layer Press with a ⅝ inch oval punch using a pressure head of 2 tons to produce a layer of the drug composition.

The driving layer of the device is formulated by mixing 75 wt % polyethylene oxide having a molecular weight of about 5,000,000 (Polyox Coag), 20 wt % NaCl, 4 wt % hydroxypropylmethyl cellulose (HPMC E-5) and 1 wt % magnesium stearate. The ingredients are mixed and added to the Manesty ® Layer Press and pressed to form a layer of hydrophylic polymer in contact with the drug layer.

A semipermeable wall is formed by blending 70 wt % cellulose acetate having an acetyl content of 39.8% with a mixture of acetone and water, 10 wt % polyethylene glycol (PEG 3350), 1 wt % sodium saccharin and 19 wt % spearmint oil. The two-layer tablet is spray coated with the cellulose acetate blend in an air suspension machine until a 6 mil thick semipermeable wall surrounds the tablet. The coated tablet is dried for 72 hours at 35° C. and then two 25 mil passageways are laser drilled through the semipermeable wall on the drug layer side of the tablet. When placed in a patient's mouth, the device immediately releases a pleasant spearmint taste.

EXAMPLE 5

An osmotic therapeutic device for the controlled and continuous release of beclomethasone dipropionate into into the oral cavity was made as follows: 0.22 mg of beclomethasone dipropionate, 167.54 mg of hydroxypropyl cellulose (KLUCEL EF), 71.76 mg of polyvinyl pyrrolidone K29-32, 0.48 mg of magnesium stearate were mixed thoroughly, resulting in a formulation with a white color.

Next, the driving layer of the device was formulated by mixing 124.8 mg of kappa-carrageenan, 22.4 mg sorbitol, 8.0 mg polyvinyl pyrrolidone K29-32, 1.6 mg potassium chloride, 1.6 mg $Fe_2O_3$ as a colorant and 1.6 mg of magnesium stearate. The hydrophilic polymer driving layer had a reddish-brown color due to the ferric oxide.

The driving layer was lightly pressed in a Manesty ® Layer Press. The beclomethasone dipropionate formulation was then added. The driving layer and the beclomethasone dipropionate formulation layer where then pressed together with a ⅝ inch oval punch using a pressure head of 2 tons to form the tablet.

Next, a semipermeable wall was formed by blending 27 g of cellulose acetate having an acetyl content of 39.8% with 1,103 ml of acetone, 100 ml of water and 18 g of polyethylene glycol 3350, and coating the two layered compartment forming member in a pan coater having a 1 kg charge until a 45 mg semipermeable wall surrounded the compartment. The coated device was dried for 72 hours at 35° C., and then one 20 mil passageway was laser drilled through the semipermeable wall to connect the layer of beclomethasone dipropionate with the exterior of the device. The KLUCEL component of the wall material made the wall sufficiently translucent to clearly see the white beclomethasone dipropionate layer and the reddish-brown hydrophilic polymer layer.

Figure 6:
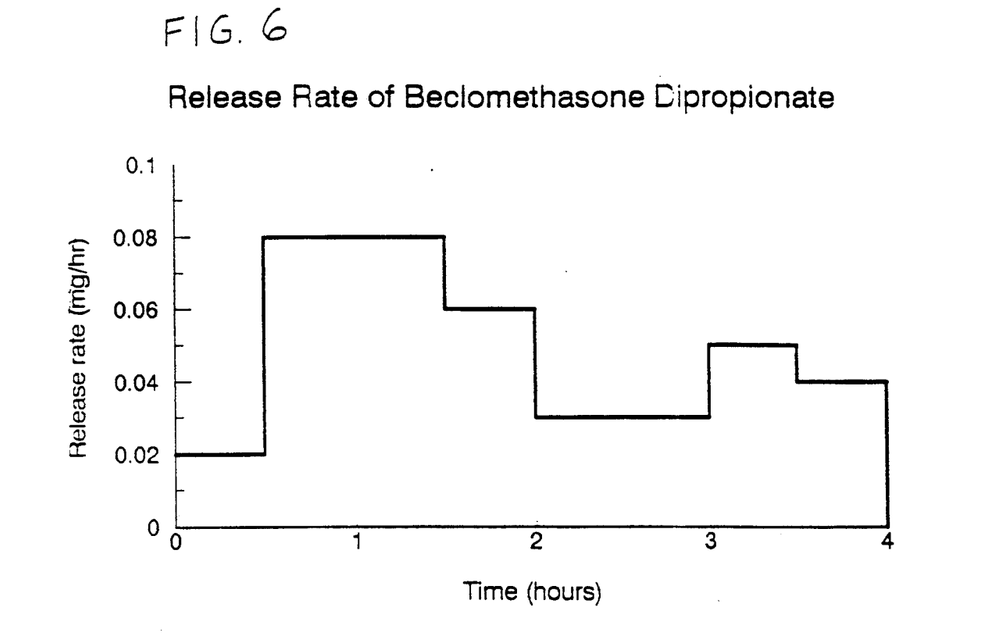
FIG. 6 is a graph depicting the release rate of beclomethasone dipropionate from a device according to the present invention.
Figure 7:
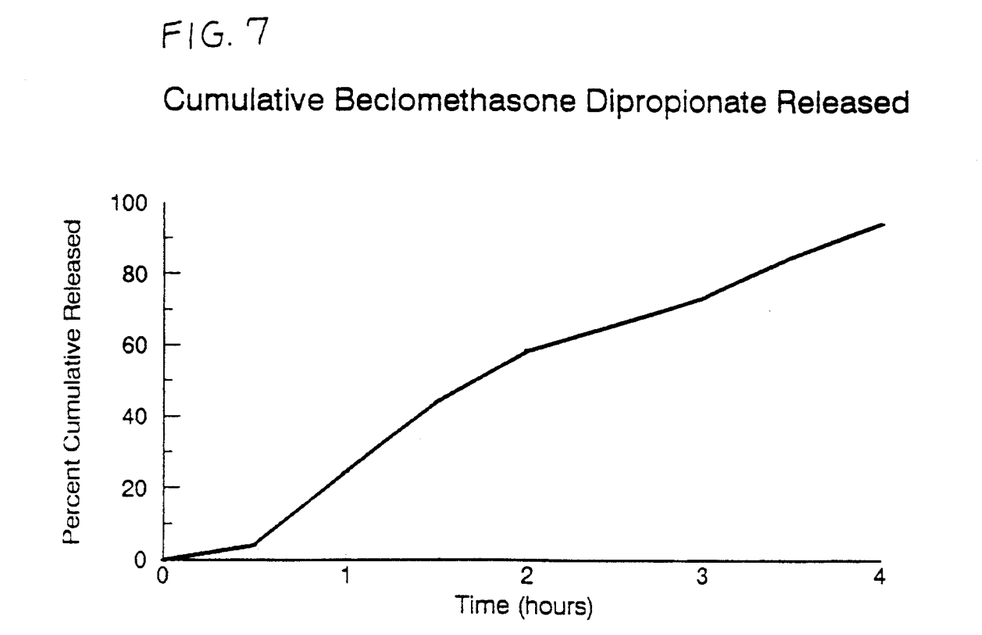
FIG. 7 is a graph depicting the cumulative amount of beclomethasone dipropionate released from a device according to the present invention.

The rate of release of the device over a four hour time period when placed in water at 37° C. is shown in FIG. 6. The cumulative amount of beclomethasone dipropionate released over the four hours from the device is shown in FIG. 7.

EXAMPLE 6

An osmotic therapeutic device manufactured in the form of an oral delivery device for delivering beclomethasone dipropionate into the oral cavity was manufactured as follows: first, a 240 mg composition comprising 0.09% beclomethasone dipropionate, 43.80% hydroxypropyl cellulose (Klucel EF), 41.06% mannitol, 10.00% polyvinyl pyrrolidone K29-32, 5.00% PGA and 0.50% magnesium stearate was prepared by blending the ingredients into a homogenous blend, and then lightly pressing the blend into a solid mass in a commercially available Manesty ® tableting machine. The resulting beclomethasone dipropionate formulation layer has a white color.

Next, a 173 mg composition containing 55.0% kappa carrageenan, 15.0% polyvinyl pyrrolidone K29-32, 28.0% sorbitol, 0.3% FD&C Blue #1, 0.07% D&C Yellow #10 and 1.0% stearic acid was blended together and added to the tableting machine. The driving layer and beclomethasone dipropionate layer were then pressed together using a ⅝ inch oval punch with a pressure head of 2 tons to form the tablet. The hydrophilic polymer layer had a green color providing a good color contrast with the white beclomethasone dipropionate containing layer.

Then, the two layered mass was coated in a standard pan coater with a semipermeable polymeric wall formed from a 4% solids solution consisting of 70 wt % cellulose acetate having an acetyl content of 39.8%, in a solvent consisting of 90% acetone and 10% water, and 30 wt % polyethylene glycol 3350. The resulting semipermeable wall had a thickness of 5 mils. The polyethylene glycol component of the wall material made the wall translucent, making it possible to see both the white beclomethasone dipropionate containing layer and the green hydrogel layer within the inner compartment of the device. Finally, one osmotic passageway, having a diameter of 20 mils, was drilled through the wall facing the beclomethasone dipropionate-containing layer for delivering it from the device.

EXAMPLE 7

An oral osmotic therapeutic device for delivering beclomethasone dipropionate is manufactured by following the procedure of Example 2, with all conditions and procedures as described, except in this example following drilling of the passageway, the device is overcoated with a mixture comprising 0.125 wt % beclomethasone dipropionate and 99.875 wt % hydroxypropylmethyl cellulose (HPMCE-5). The overcoating layer has a thickness of 3 mils.

The beclomethasone dipropionate overcoat provides a loading dose which is quickly delivered to the patient upon retention in the mouth. Generally, the overcoat layer is completely removed by patient sucking within about 15 to 30 minutes.

While certain preferred embodiments of the invention have been described in detail herein, those skilled in the art will appreciate that numerous modifications of the described embodiments can be made without departing from the spirit and scope of the invention as defined in the appended claims.

We claim:

1. An osmotic device for the controlled delivery of beclomethasone dipropionate to an oral cavity of an animal over an extended delivery period, the device having a size and shape suitable for comfortably retaining the device in the oral cavity for the extended delivery period, the device including a wall surrounding and forming a compartment containing (i) a layer of beclomethasone dipropionate and a gelling agent, and (ii) a layer of a hydrophilic polymer, and a passageway in the semipermeable wall communicating with the layer of beclomethasone dipropionate in the compartment and with the exterior of the device, the wall being formed of a semipermeable material which is (i) permeable to the passage of the aqueous fluid and (ii) substantially impermeable to the passage of the hydrophilic polymer;
   the device further comprising a mechanism for signaling the animal when the dose of beclomethasone dipropionate has been delivered from the device, the mechanism including a contrast in the colors of the beclomethasone dipropionate layer and the hydrophilic polymer layer.

2. The osmotic device for the controlled delivery of beclomethasone dipropionate according to claim 1, wherein the mechanism comprises means for displaying the amount of beneficial agent present in the device.

3. The osmotic device for the controlled delivery of beclomethasone dipropionate according to claim 1, wherein the semipermeable wall is sufficiently translucent to permit visual inspection of the beclomethasone dipropionate present in the compartment during substantially all of the extended delivery period.

4. The osmotic device for the controlled delivery of beclomethasone dipropionate according to claim 3, wherein the semipermeable wall has an overcoating containing beclomethasone dipropionate.

5. The osmotic device for the controlled delivery of beclomethasone dipropionate according to claim 1, wherein the device has a smooth oval shape with an aspect ratio in the range of about 1.2:1 to about 3:1, a height of about 0.5 to about 10 mm, and a volume of less than about 2 cm$^3$.

6. The osmotic device for the controlled delivery of beclomethasone dipropionate according to claim 1, wherein the layer of beclomethasone dipropionate contains an osmagent.

7. The osmotic device for the controlled delivery of beclomethasone dipropionate according to claim 1, wherein the gelling agent provides sufficient strength to the layer containing the beclomethasone dipropionate to substantially prevent the wall from collapsing under conditions of use in the oral cavity.

8. The osmotic device for the controlled delivery of beclomethasone dipropionate according to claim 1, wherein the gelling agent is selected from the group consisting of acacia, agar-agar, calcium carrageenan, kappa carrageenan, alginic acid, algin, agarose powder, collagen, colloidal magnesium silicate, colloidal silicon dioxide, cross-linked polyacrylic acid, polyvinyl pyrrolidone, sodium carboxymethyl cellulose, hydroxyethyl cellulose, hydroxypropyl cellulose, hydroxypropylmethyl cellulose, polyethylene oxide, pectin, gelatin and calcium silicate.

9. The osmotic device for the controlled delivery of beclomethasone dipropionate according to claim 8, wherein the gelling agent is hydroxypropyl cellulose, polyvinyl pyrrolidone or kappa carrageenan.

10. The osmotic device for the controlled delivery of beclomethasone dipropionate according to claim 1, wherein the wall contains a translucent cellulose polymer.

11. The osmotic device for the controlled delivery of beclomethasone dipropionate according to claim 1, wherein the hydrophilic polymer is a cross-linked hydrogel.

12. An osmotic device for the controlled delivery of beclomethasone dipropionate to an oral cavity of an animal over an extended delivery period, the device having a size and shape suitable for comfortably retaining the device in the oral cavity for the extended delivery period, the device including a wall surrounding and forming a compartment containing (i) a dose of beclomethasone dipropionate formulation which comprises beclomethasone dipropionate, an osmotically effective solute that is soluble in the exterior fluid and exhibits an osmotic pressure gradient across the wall against the fluid and a gelling agent, and (ii) a layer of a hydrophilic polymer, and a passageway in the semipermeable wall communicating with the layer of beclomethasone dipropionate in the compartment and with the exterior of the device, the wall being formed of a semipermeable material which is (i) permeable to the passage of the aqueous fluid and (ii) substantially impermeable to the passage of the hydrophilic polymer;

the device further comprising a mechanism for signaling the animal when the dose of beclomethasone dipropionate has been delivered from the device, the mechanism including a contrast in the colors of the beclomethasone dipropionate layer and the hydrophilic polymer layer.

13. The osmotic device for the controlled delivery of beclomethasone dipropionate according to claim 12, wherein the mechanism comprises means for displaying the amount of beclomethasone dipropionate formulation present in the device.

14. The osmotic device for the controlled delivery of beclomethasone dipropionate according to claim 12, wherein the semipermeable wall is sufficiently translucent to permit visual inspection of the layer of beclomethasone dipropionate formulation present in the compartment during substantially all of the extended delivery period.

15. The osmotic device for the controlled delivery of beclomethasone dipropionate according to claim 12, wherein the semipermeable wall has an overcoating containing beclomethasone dipropionate.

16. The osmotic device for the controlled delivery of beclomethasone dipropionate according to claim 15, wherein the semipermeable wall is sufficiently translucent to permit visual inspection of the layer of beclomethasone dipropionate formulation present in the compartment after the overcoating is removed.

17. The osmotic device for the controlled delivery of beclomethasone dipropionate according to claim 12, wherein the device has a smooth oval shape with an aspect ratio in the range of about 1.2:1 to about 3:1, a height of about 0.5 to about 10 mm, and a volume of less than about 2 $cm^3$.

18. The osmotic device for the controlled delivery of the beclomethasone dipropionate formulation according to claim 12, wherein the gelling agent provides sufficient strength to the beclomethasone formulation to substantially prevent the wall from collapsing under conditions of use in the oral cavity.

19. The osmotic device for the controlled delivery of the beclomethasone dipropionate formulation according to claim 18, wherein the gelling agent is selected from the group consisting of acacia, agar-agar, calcium carrageenan, kappa carrageenan, alginic acid, algin, agarose powder, collagen, colloidal magnesium silicate, colloidal silicon dioxide, carboxy methyl cellulose, cross-linked polyacrylic acid, polyvinyl pyrrolidone, hydroxy ethyl cellulose, hydroxy propyl cellulose, hydroxy propyl methyl cellulose, polyethylene oxide, pectin, gelatin and calcium silicate.

20. The osmotic device for the controlled delivery of the beclomethasone dipropionate formulation according to claim 19, wherein the gelling agent is hydroxypropyl cellulose, polyvinyl pyrrolidone or kappa carrageenan.

21. The osmotic device for delivering beclomethasone dipropionate according to claim 12, wherein the hydrophilic polymer is a cross-linked hydrogel.

22. The osmotic device of claim 1 or 12, wherein the device has an aspect ratio of about 1.3:1 to 2:1.

23. The osmotic device of claim 1 or 12, wherein the device has an aspect ratio of about 1.5:1 to 1.7:1.

24. The osmotic device of claim 1 or 12, wherein the device has a height of about 2 to 8 mm.

25. The osmotic device of claim 1 or 12, wherein the device has a volume of about 0.1 to 0.5 $cm^3$.

26. The osmotic device of claim 1 or 12, wherein the extended delivery period is about 0.5 to 12 hours.

27. The osmotic device of claim 1 or 12, wherein the extended delivery period is about 1 to 6 hours.

28. The osmotic device of claim 1 or 12, wherein the semipermeable wall has a mark indicating when a predetermined percentage of beclomethasone dipropionate has been delivered into the oral cavity.

* * * * *